United States Patent
Yang et al.

(10) Patent No.: US 9,228,995 B2
(45) Date of Patent: Jan. 5, 2016

(54) METHOD AND APPARATUS FOR MEASURING HEMATOCRIT OF BLOOD

(71) Applicant: GWANGJU INSTITUTE OF SCIENCE AND TECHNOLOGY, Gwangju (KR)

(72) Inventors: Sung Yang, Gwangju (KR); Myounggon Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/301,782

(22) Filed: Jun. 11, 2014

(65) Prior Publication Data

US 2015/0260705 A1 Sep. 17, 2015

(30) Foreign Application Priority Data

Mar. 12, 2014 (KR) .................. 10-2014-0028721

(51) Int. Cl.
| | |
|---|---|
| *G01N 27/06* | (2006.01) |
| *G01N 33/49* | (2006.01) |
| *G01N 27/02* | (2006.01) |
| *G01N 27/08* | (2006.01) |
| *G01N 27/07* | (2006.01) |

(52) U.S. Cl.
CPC ............... *G01N 33/49* (2013.01); *G01N 27/02* (2013.01); *G01N 27/06* (2013.01); *G01N 27/07* (2013.01); *G01N 27/08* (2013.01)

(58) Field of Classification Search
CPC ..... G01N 33/48; G01N 33/49; G01N 33/491; G01N 33/50; G01N 33/5002; G01N 33/80; G01N 27/02; G01N 27/04; G01N 27/06; G01N 27/07; G01N 27/08; Y10T 436/2575

USPC ............ 436/63, 70, 149, 150, 151, 180; 422/68.1, 73, 82.01, 82.02, 502, 503
See application file for complete search history.

(56) References Cited

U.S. PATENT DOCUMENTS

| | | | | |
|---|---|---|---|---|
| 4,547,735 A | * | 10/1985 | Kiesewetter et al. | 324/450 |
| 2012/0111739 A1 | * | 5/2012 | Pasqua et al. | 205/777.5 |
| 2013/0110405 A1 | * | 5/2013 | Yang et al. | 702/19 |

FOREIGN PATENT DOCUMENTS

KR    1020130046143 A    5/2013

OTHER PUBLICATIONS

Kim et al. Biosensors and Bioelectronics, vol. 35, Feb. 14, 2012, pp. 416-420.*

(Continued)

*Primary Examiner* — Maureen Wallenhorst
(74) *Attorney, Agent, or Firm* — Hauptman Ham, LLP (57) ABSTRACT

Disclosed herein are a method and an apparatus for measuring hematocrit of flowing blood. The apparatus for measuring hematocrit of blood according to an exemplary embodiment of the present invention includes: a body part provided with a blood inlet and a blood outlet; first and second electrodes disposed on both inner side walls of the body part so as to be opposite to each other; a third electrode disposed on the same side wall as a side wall on which the first electrode is disposed while maintaining a predetermined distance from the first electrode; a measurement unit measuring first impedance of blood between the first and second electrodes and second impedance of the blood between the first and third electrodes; and a calculation unit determining the hematocrit of blood using the first and second impedances.

2 Claims, 9 Drawing Sheets

(56) References Cited

OTHER PUBLICATIONS

Myounggon Kim et al., Study on critical parameters for a continuous hematocrit measurement of blood flow, article, Apr. 5, 2013, pp. 165-166, The 15th Korean Micro Electro Mechanical Systems.

M. Kim et al., Study on the continuous hematocrit measurement under various blood flow conditions, poster and article, Nov. 8, 2013, 2013 Fall Scholarship Seminar of the Korean Society of medical & Biological Engineering.

Korean Office Action issued on Sep. 9, 2015 in connection with the counterpart Korean Patent Application No. 10-2014-0028721.

\* cited by examiner

METHOD AND APPARATUS FOR MEASURING HEMATOCRIT OF BLOOD

CROSS REFERENCE TO RELATED APPLICATION

This application claims the benefit of Korean Patent Application NO. 10-2014-0028721, filed on Mar. 12, 2014, entitled "Method and Apparatus for Measuring Hematocrit of Blood", which is hereby incorporated by reference in its entirety into this application.

BACKGROUND OF THE INVENTION

1. Technical Field

The present invention relates to a method and an apparatus for measuring hematocrit of blood.

2. Description of the Related Art

Hematocrit (HCT) refers to a volume percent of red blood cells in blood, and more particularly, to a relative volume of red blood cells to a volume of blood. In the case of using the hematocrit, since it is possible to know a volume ratio between blood cell components and blood plasma components, information associated with an oxygen amount in blood such as information on anemia may be obtained.

According to the related art, hematocrit of blood is measured using various methods. As a relative simple measuring method, there is a centrifugation method. In the case in which injecting a blood sample in a glass capillary tube and rapidly rotating the glass capillary tube at a high speed, a red blood component in the blood is separated from plasma to form a layer. In this case, a height of the red blood cell layer with respect to the entire height of the blood sample in the capillary tube is measured, thereby obtaining hematocrit. However, in this method, a relatively long time is consumed to measure the hematocrit, and it is impossible to perform hematocrit measurement on flowing blood in real-time.

As another method, the hematocrit may be measured using a Coulter counter. The Coulter counter is a device for measuring a change in electric impedance shown when particles passes through a fine pore, and an average volume percent and the number of individual red cells may be measured using the Coulter counter. However, the Coulter counter is expensive and has a large volume, and it is difficult to carry the Coulter counter.

In the case of electrically measuring hematocrit of flowing blood using the Coulter counter, impedance of blood is changed according to a state of plasma and a change in flow rate, which causes a measuring error of hematocrit. Therefore, a method for measuring hematocrit capable of considering a flow rate as well as a change in a plasma state has been required.

SUMMARY OF THE INVENTION

The present invention has been made in an effort to provide a method and an apparatus for measuring hematocrit of flowing blood capable of more simply and accurately measuring hematocrit of flowing blood in real time.

Objects of the present inventions are not limited to the above-mentioned object, and other objects and advantages of the present invention can be appreciated by the following description and will be clearly described by the embodiments of the present invention. Further, it will be easily known that the objects and advantages of the present invention can be implemented by means and a combination thereof shown in the appended claims.

According to an exemplary embodiment of the present invention, there is provided an apparatus for measuring hematocrit of blood including: a body part provided with a blood inlet and a blood outlet; first and second electrodes disposed on both inner side walls of the body part so as to be opposite to each other; a third electrode disposed on the same side wall as a side wall on which the first electrode is disposed while maintaining a predetermined distance from the first electrode; a measurement unit measuring first impedance of blood between the first and second electrodes and second impedance of the blood between the first and third electrodes; and a calculation unit determining hematocrit of the blood using the first and second impedances.

According to another exemplary embodiment of the present invention, there is provided a method for measuring hematocrit of blood including: measuring first impedance of blood between first and second electrodes disposed on both inner side walls of a body part so as to be opposite to each other; measuring second impedance of the blood between the first electrode and a third electrode disposed on the same side wall as the side wall on which the first electrode is disposed while maintaining a predetermined distance from the first electrode; and determining hematocrit of the blood using the first and second impedances.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

The above objects, features, and advantages will be described in detail with reference to the accompanying drawings and therefore, the technical ideas of the present invention can be easily practiced by a person with ordinary skill in the art to which the present invention pertains. Further, when it is determined that the detailed description of the known art related to the present invention may obscure the gist of the present invention, the detailed description thereof will be omitted. Hereinafter, exemplary embodiments of the present invention will be described in detail with reference to the accompanying drawings. Throughout the disclosure, like reference numerals refer to like parts throughout the various figures and embodiments of the present invention.

Figure 1:
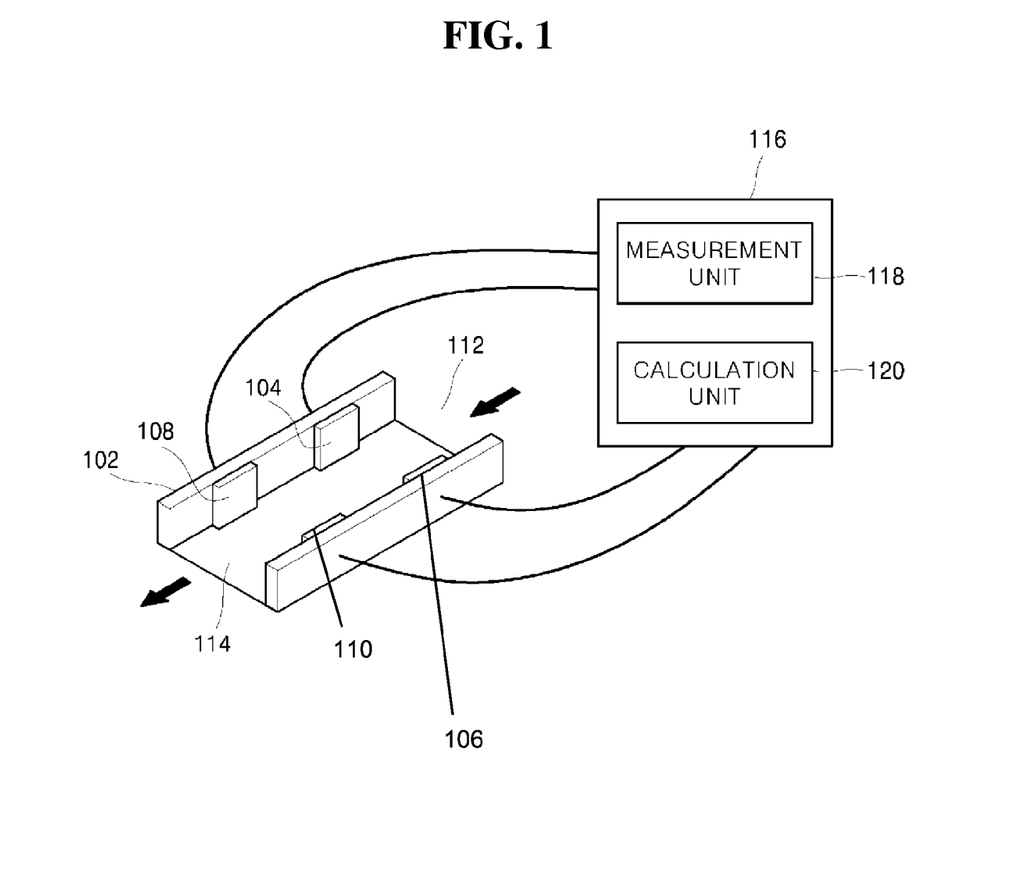
FIG. 1 is a configuration diagram of an apparatus for measuring hematocrit of blood according to an exemplary embodiment of the present invention.

FIG. 1 is a configuration diagram of an apparatus for measuring hematocrit of blood according to an exemplary embodiment of the present invention.

Referring to FIG. 1, the apparatus for measuring hematocrit of blood according to the exemplary embodiment of the present invention includes a body part 102 and a measurement-calculation unit 116. The body part 102 is provided with a blood inlet 112 and a blood outlet 114. Blood introduced through the blood inlet 112 passes between electrodes 104, 106, 108, and 110 in the body part 102 and then is discharged to the outside through the blood outlet 114.

A first electrode 104, a second electrode 106, a third electrode 108, and a fourth electrode 110 are respectively formed in the body part 102. The first and second electrodes 104 and 106 are disposed on both inner side walls of the body part 102 so as to be opposite to each other. Similarly, the third and fourth electrodes 108 and 110 are disposed on both inner side walls of the body part 102 so as to be opposite to each other. As shown in FIG. 1, the first and third electrodes 104 and 108 are disposed on the same side wall as each other while maintaining a predetermined distance therebetween. In addition, the second and fourth electrodes 106 and 110 are also disposed on the same side wall as each other while maintaining a predetermined distance therebetween.

The first electrode 104, the second electrode 106, the third electrode 108, and the fourth electrode 110 are connected to the measurement-calculation unit 116 through wires, respectively. The measurement-calculation unit 116 includes a measurement unit 118 and a calculation unit 120.

The measurement unit 118 may select two electrodes from four electrodes 104, 106, 108, and 110 connected by the wire and measure impedance of blood flowing between the selected two electrodes. In the exemplary embodiment of the present invention, impedance of blood measured in the measurement unit 118 includes first impedance and second impedance.

The first impedance means impedance of blood measured between a pair of opposite electrodes (OE) in the body part 102. For example, the measurement unit 118 may measure impedance of blood flowing between the first and second electrodes 104 and 106 as the first impedance. In addition, the measurement unit 118 may measure impedance of blood flowing between the third and fourth electrodes 108 and 110 as the first impedance. Plasma and cytoplasm are contained in the blood flowing between the selected two electrodes, and the first impedance includes impedance of plasma and impedance of cytoplasm.

The second impedance means impedance of blood measured between two longitudinal electrodes (LE) formed on the same side wall of the body part 102. For example, the measurement unit 118 may measure impedance of blood flowing between the first and third electrodes 104 and 108 as the second impedance. In addition, the measurement unit 118 may measure impedance of blood flowing between the second and fourth electrodes 106 and 110 as the second impedance. Plasma and cytoplasm are contained in the blood flowing between the selected two electrodes, and the second impedance includes impedance of plasma and impedance of cytoplasm.

The calculation unit 120 determines hematocrit of blood passing through the inside of the body part 102 using the first and second impedance of blood measured in the measurement unit 118.

In the exemplary embodiment of the present invention, the calculation unit 120 calculates a first hematocrit estimation parameter $\text{HEP}_{OE}$ using the first impedance and calculates a second hematocrit estimation parameter $\text{HEP}_{LE}$ using the second impedance. The first hematocrit estimation parameter $\text{HEP}_{OE}$ is determined by a ratio of impedance $R_{p1}$ of plasma included in the first impedance and a sum of impedance $R_{p1}$ of plasma and impedance $R_{i1}$ of cytoplasm. Further, the second hematocrit estimation parameter $\text{HEP}_{LE}$ is determined by a ratio of impedance $R_{p2}$ of plasma included in the second impedance and a sum of impedance $R_{p2}$ of plasma and impedance $R_{i2}$ of cytoplasm.

The calculation unit 120 determines a normalized difference (ND) using the calculated first and second hematocrit estimation parameters $\text{HEP}_{OE}$ and $\text{HEP}_{LE}$. Then, the calculation unit 120 determines hematocrit of blood passing through the inside of the body part 102 using the first hematocrit estimation parameter $\text{HEP}_{OE}$ and normalized difference (ND).

Hereinafter, a method for measuring hematocrit of blood according to an exemplary embodiment of the present invention will be described in detail with reference to FIG. 1.

In an electric measurement method used in order to measure hematocrit of blood according to the related art, the following Equation is satisfied.

$$\sigma_{whole\ blood} = \text{fn}(\text{Hct}, \sigma_{plasma}, \pi_{plasma}) \qquad \text{[Equation 1]}$$

As shown in [Equation 1], in the case of the method for electrically measuring hematocrit (HCT) according to the related art, electric conductivity $\sigma_{whole\ blood}$ of blood is affected by HCT, electric conductivity $\sigma_{plasma}$ of plasma, and osmotic pressure $\pi_{plasma}$ of plasma. Therefore, there are disadvantages in that it is not easy to confirm whether the change in electric parameters of blood is caused by a change in HCT of blood or by a change in plasma, and at the time of measuring HCT, a measurement error may be increased. Therefore, in the present invention, a HCT estimation parameter (HEP), which is a new parameter, is used in order to measure hematocrit using only electric conductivity of blood regardless of electric conductivity of plasma or osmotic pressure of plasma.

Figure 2:
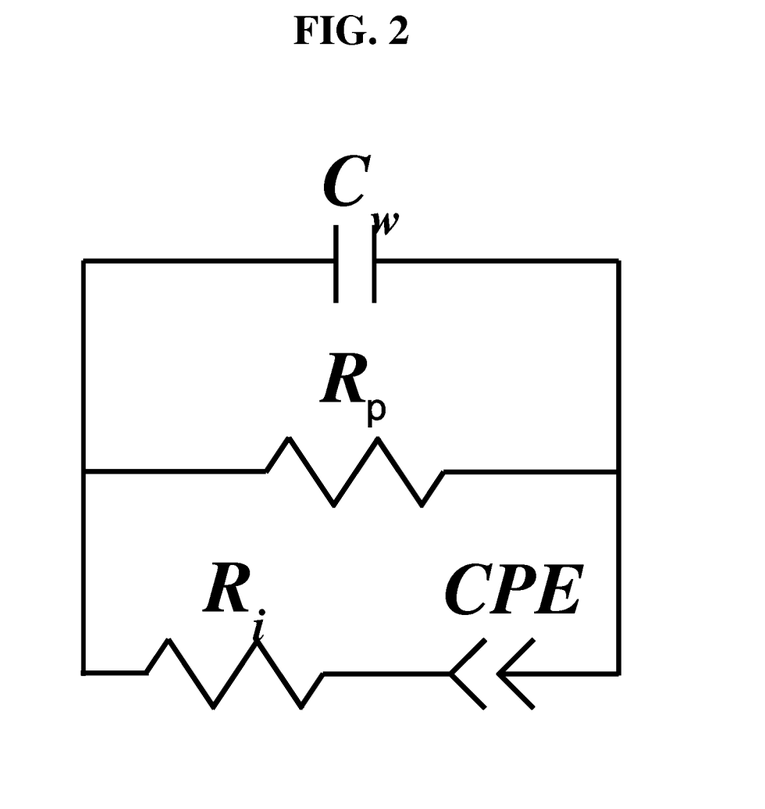
FIG. 2 is a diagram showing a lumped parameter modeling of blood that is, electric modeling of blood.

FIG. 2 is a diagram showing a lumped parameter modeling of blood that is, electric modeling of blood.

In FIG. 2, $R_p$ means impedance of plasma, and $R_i$ means impedance of cytoplasm. In addition, $C_w$ means capacitance indicating a change in impedance of blood generated by rearrangement of water molecules present in plasma according to the change in frequency. CPE (Constant Phase Element), which represents frequency response characteristics of blood having characterstics of a heterogeneous material composed of liquid and solid, means dielectric dispersion in the frequency response of a plurality of red blood cells and plasma, that capacitance changed according to the frequency.

$$Z_{CPE} = \frac{1}{C(\omega j)^\alpha} \quad \text{[Equation 2]}$$

Impedance $Z_{CPE}$ of the CPE may be defined by Equation 2, wherein C is a constant which denotes the intensity of CPE. In [Equation 2], "ω" represents a change in the frequency and "j" is a complex number. "ω" and "j" are variables adjusted according to characteristics of frequencies. "α" represents a degree of dielectric dispersion by a plurality cells, or surface roughness of the cells. The surface roughness tends to increase with decreasing value of α ($\omega=2\pi f$, $0<\alpha<1$).

The impedance of blood differs according to conditions. For example, impedances of blood contained in hypotonic, isotonic, mannitol, and aqueous NaCl solutions may be different from each other.

Figure 3:
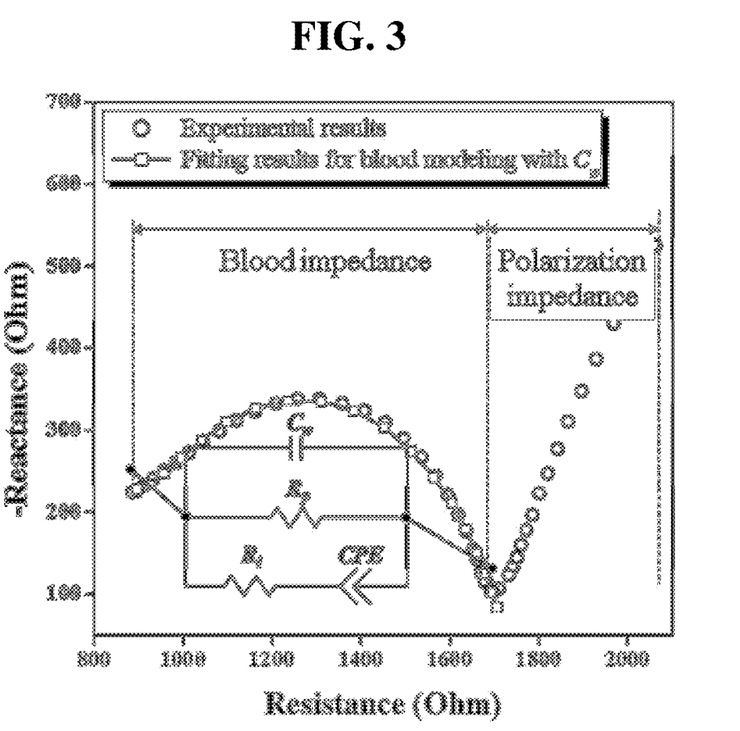
FIG. 3 is a graph showing a change in impedance shown through electric modeling of blood according to the related art.

FIG. 3 is a graph showing impedance and reactance of blood according to the frequencies, which shows a change in impedance in electrical modeling of blood according to the related art. That is, a impedance zone may be divided into a blood impedance zone and an electrode polarization impedance zone. A solid line indicates impedance data obtained through a impedance data measurement unit, and a dotted line indicates results obtained by fitting the blood impedance zone through electrical modeling. For example, while the frequency is changed from a low frequency of 1 kHz into a high frequency of 10 MHz, the electrode impedance gradually decreases, and when the frequency is changed from 80 kHz into 10 MHz, the impedance gradually decreases and the reactance increases or decreases according to the phase of the frequency.

In order to determine the estimation parameter used in the present invention, impedance of blood flowing between two electrodes may be modeled as follows.

$$R = \rho \frac{L}{A} \quad \text{[Equation 3]}$$

In [Equation 3], ρ means impedance coefficient of blood, L means a distance between two electrodes, and A means a contact area between blood and the electrode. However, when a volume V of the blood flowing between two electrodes decreases, since ρ and L are constants that are not changed, R is changed by an influence of A. That is, when the volume V decreases, the contact area A between blood and the electrode decreases, and impedance R increases in accordance with the decrease in the contact area A.

Therefore, the impedance $R_p$ of plasma may be modeled with an inverse number of a volume $V_p$ of plasma, and impedance $R_i$ of cytoplasm may be modeled with an inverse number of a volume $V_R$ of red blood cells (RBCs).

$$\frac{V_R}{V_P + V_R} \cdot 100(\%) \approx \frac{\frac{1}{R_i}}{\frac{1}{R_P} + \frac{1}{R_i}} \cdot 100(\%) = \frac{R_P}{R_i + R_P} \cdot 100(\%) \quad \text{[Equation 4]}$$

Therefore, the hematocrit estimation parameter (HEP) may be defined as follows.

$$HEP = 100 \cdot \frac{R_P}{R_i + R_P} \quad \text{[Equation 5]}$$

That is, as shown in [Equation 5], the hematocrit estimation parameter is defined as a ratio of impedance $R_p$ of plasma and a sum ($R_i+R_P$) of impedance of plasma and impedance of cytoplasm.

In order to determine the hematocrit estimation parameter, the measurement unit 118 of FIG. 1 measures each of the first and second impedances. For example, the measurement unit 118 measures first impedance between a pair of opposite electrodes, that is, the first and second electrodes 104 and 106. However, in another exemplary embodiment of the present invention, the measurement unit 118 may measure first impedance between the third and fourth electrodes 108 and 110. The measured first impedance includes impedance $R_{p1}$ of plasma contained in measurement target blood and impedance $R_{i1}$ of cytoplasm contained in measurement target blood.

In addition, the measurement unit 118 measures second impedance between two longitudinal electrodes formed on the same side wall as each other, for example, the first and second electrodes 104 and 108. However, in another exemplary embodiment of the present invention, the measurement unit 118 may also measure second impedance between the second and fourth electrodes 106 and 110. The measured second impedance includes impedance $R_{p2}$ of plasma contained in measurement target blood and impedance $R_{i2}$ of cytoplasm contained in measurement target blood.

The calculation unit 120 may calculate each of the first and second hematocrit estimation parameters $HEP_{OE}$ and $HEP_{LE}$ by substituting first impedances $R_{p1}$ and $R_{i1}$ and second impedances $R_{p2}$ and $R_{i2}$ measured by the measurement unit 118 in [Equation 5].

$$HEP_{OE} = \frac{R_{p1}}{R_{i1} + R_{p1}} \times 100 \quad \text{[Equation 6]}$$

$$HEP_{LE} = \frac{R_{p2}}{R_{i2} + R_{p2}} \times 100$$

Figure 4:
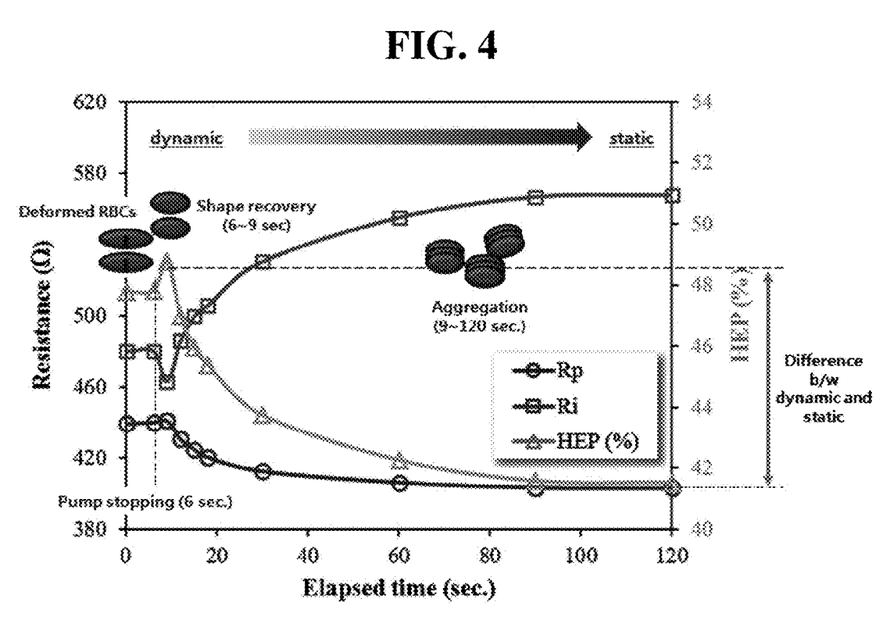
FIG. 4 is a graph showing a change in red blood cells shown when blood is changed from a dynamic state into a static state and changes in impedance $R_{p1}$ of plasma, impedance $R_{i1}$ of red blood cells, and hematocrit estimation parameter (HEP) according to the change in red blood cells.

Meanwhile, in the present invention, hematocrit of blood is determined in consideration onf a shear rate of blood determined according to a flow rate of blood. When blood flows, cytoplasm such as red blood cells contained in blood may be aggregated with each other, deformed, or arranged so as to have a specific structure. The shear rate of blood is changed by aggregation, deformation, or arrangement of cytoplasm as described above, and thus, impedance of blood is changed, such that hematocrit are also changed. FIG. 4 is a graph showing a change in red blood cells shown when blood is changed from a dynamic state into a static state and changes in impedance $R_{p1}$ of plasma, impedance $R_{i1}$ of red blood cells, and hematocrit estimation parameter (HEP) according to the change in red blood cells.

Figure 5:
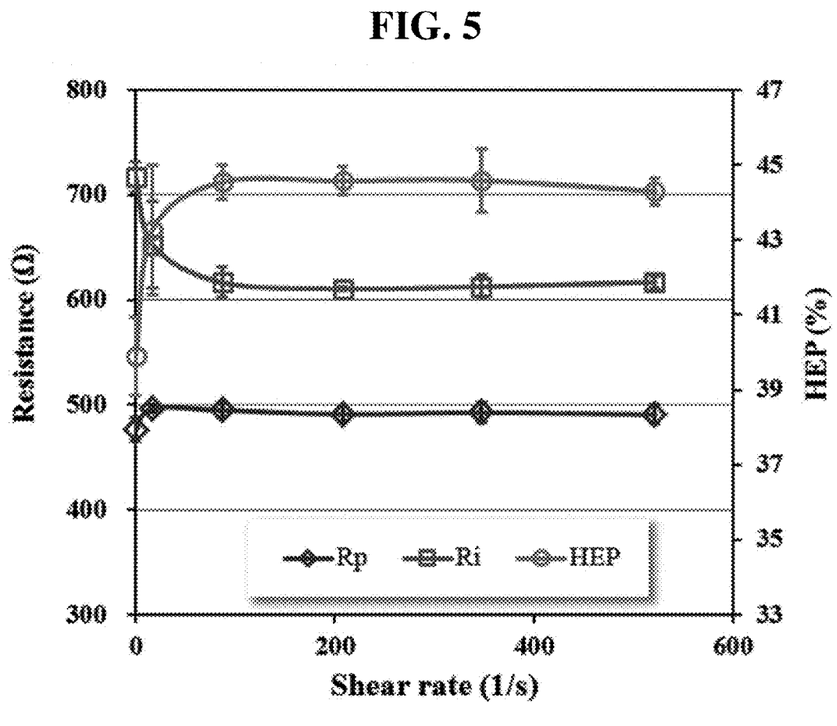
FIG. 5 is a graph showing changes in impedance $R_{p1}$ of plasma, impedance $R_{i1}$ of red blood cells, and a first hematocrit estimation parameter (HEP) according to a change in a shear rate of measurement target blood.
Figure 6:
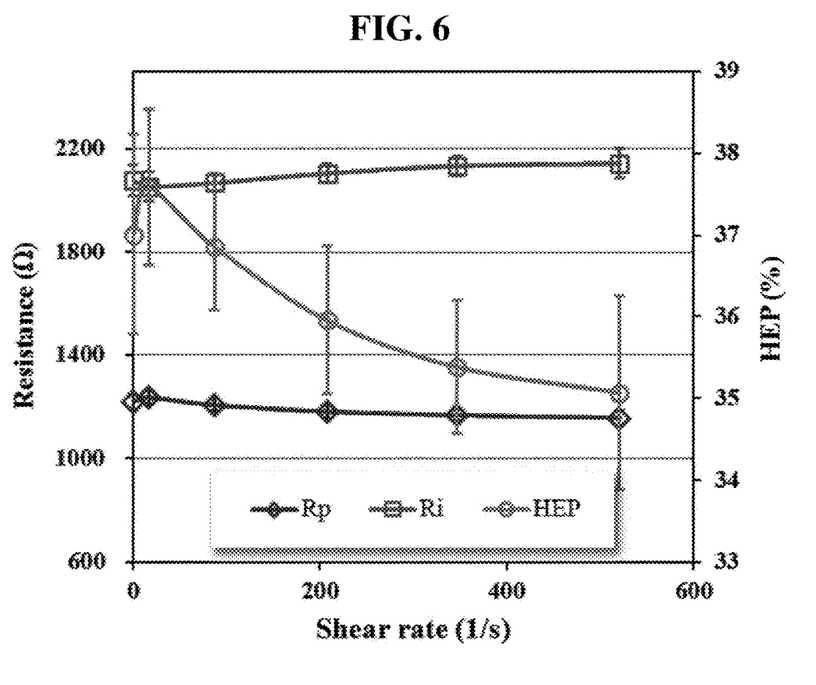
FIG. 6 is a graph showing changes in impedance $R_{p2}$ of plasma, impedance $R_{i2}$ of red blood cells, and a second hematocrit estimation parameter (HEP) according to a change in a shear rate of measurement target blood.

The previously calculated first and second hematocrit estimation parameters are also changed in accordance with the change in shear rate of blood as described above while having different tendencies from each other. FIG. 5 is a graph showing changes in impedance $R_p$ of plasma, impedance $R_{i1}$ of red blood cells, and first hematocrit estimation parameter HEP according to a change in a shear rate of measurement target blood, and FIG. 6 is a graph showing changes in impedance $R_p$ of plasma, impedance $R_i$ of red blood cells, and a second hematocrit estimation parameter HEP according to a change in a shear rate of measurement target blood.

Therefore, the calculation part 120 of the present invention calculates the normalized difference (ND) using the calculated first hematocrit estimation parameter ($HEP_{OE}$) and second hematocrit estimation parameter ($HEP_{LE}$) as follows.

$$ND = \frac{HEP_{OE} - HEP_{LE}}{HEP_{OE}} \quad \text{[Equation 7]}$$

Figure 7:
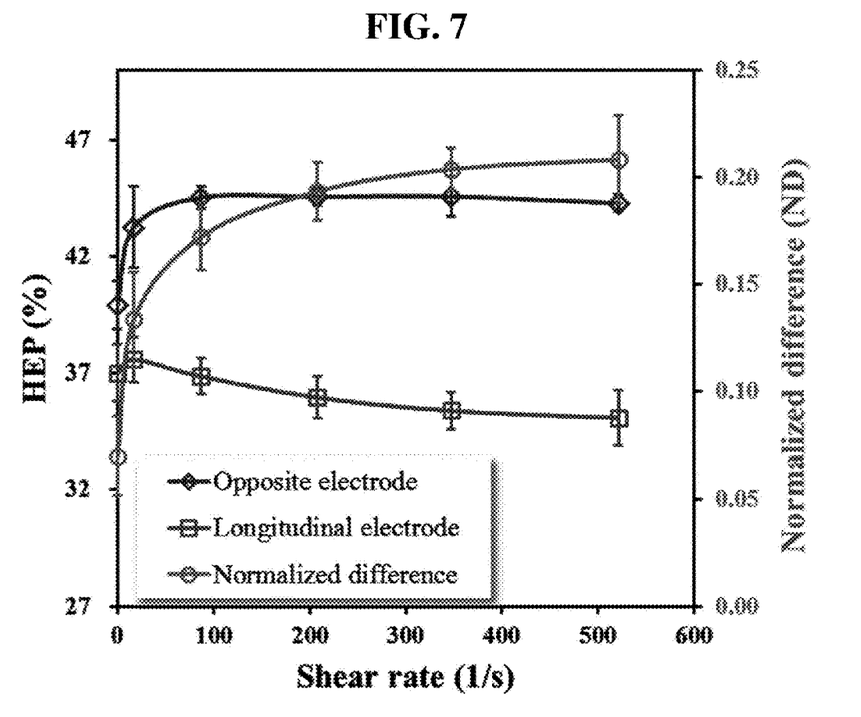
FIG. 7 is a graph showing changes in a first hematocrit estimation parameter $HEP_{OE}$, a second hematocrit estimation parameter $HEP_{LE}$, and a normalized difference (ND) between the first hematocrit estimation parameter $HEP_{OE}$ and the second hematocrit estimation parameter $HEP_{LE}$ according to a change in a shear rate of measurement target blood.

FIG. 7 is a graph showing changes in a first hematocrit estimation parameter (represented by opposite electrode in FIG. 7) a second hematocrit estimation parameter (represented by longitudinal electrode in FIG. 7), and a normalized difference (ND) between the first hematocrit estimation parameter and the second hematocrit estimation parameter according to a change in a shear rate of measurement target blood.

The calculation unit 120 determines hematocrit of measurement target blood using the calculated normalized difference (ND) and the first hematocrit estimation parameter $HEP_{OE}$. In the exemplary embodiment of the present invention, the calculation unit 120 calculates hematocrit HCTmeas of the measurement target blood using the following Equation.

$$HCT_{meas} = a + b \cdot HEP_{OE} - c \cdot ND \quad \text{[Equation 8]}$$

In the present invention, Relation Equation such as [Equation 8] may be obtained by linear-fitting of hematocrit of individual test blood samples for a plurality of different test blood samples with hematocrit estimation parameters and normalized difference for the individual test blood samples. In [Equation 8], a, b, and c are constants determined by the above-mentioned linear fitting. In the exemplary embodiment of the present invention, the hematocrit HCTmeas of the measurement target blood may be determined by 4.58+0.909·HEP−35.7·ND.

In [Equation 8], the hematocrit estimation parameter $HEP_{OE}$ is a factor for considering electric characteristics of plasma, and the normalized difference (ND) is a value for considering the change in the hematocrit estimation parameter generated according to the change in the shear rate of blood. As a result, in the present invention, hematocrit of flowing blood may be accurately measured by simultaneously considering two parameters, that is, the hematocrit estimation parameter and the normalized difference.

The above-mentioned apparatus for measuring hematocrit according to the present invention may more easily measure hematocrit of flowing blood as compared to the electric measurement method according to the related art. Further, since a difference between the hematocrit measured by the apparatus for measuring hematocrit according to the present invention and the hematocrit measured by the electric measurement method according to the related art is not large, the apparatus for measuring hematocrit according to the present invention has an advantage in that relatively accurate hematocrit may be easily obtained.

In order to judge accuracy of the apparatus for measuring hematocrit according to the present invention, reference hematocrit HCTref measured by the method according to the related art and hematocrit HCTmeas measured by the apparatus for measuring hematocrit according to the present invention may be compared with each other. For example, first and second impedances of each of the six blood samples having different flow rate conditions from each other are measured, and then first and second hematocrit estimation parameters may be calculated using the measured first and second impedances. Further, a normalized difference of each of the samples is calculated, and hematocrit HCTmeas of each of the six blood samples may be determined using the calculated normalized difference and first hematocrit estimation parameter.

The following measurement error (Error) may be calculated using the hematocrit HCTmeas of each of the six blood samples determined as described above and reference hematocrit HCTref measured by the method according to the related art.

$$\text{Error}(\%) = \left| \frac{HCT_{meas.} - HCT_{ref.}}{HCT_{ref.}} \right| \times 100 \quad \text{[Equation 9]}$$

Figure 8:
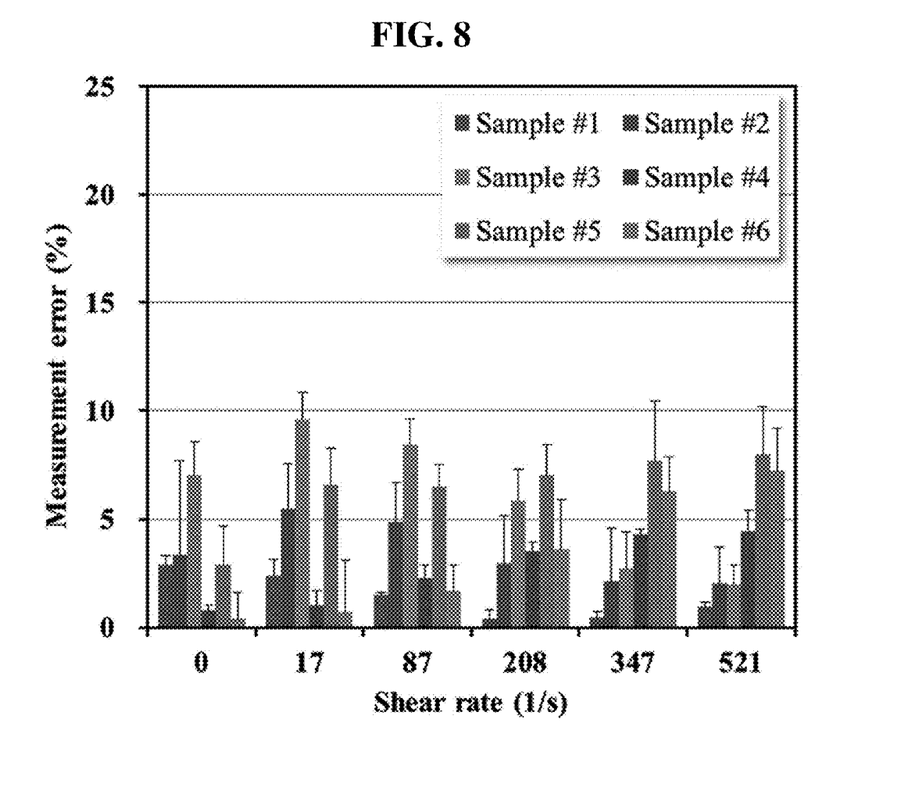
FIG. 8 is a graph showing measurement errors between hematocrit of blood samples #1 to #6 having different electric properties from each other measured using a suggested method under different flow rate conditions and reference hematocrit.

FIG. 8 is a graph showing measurement errors between hematocrit of blood samples #1 to #6 having different electric properties from each other measured using a suggested method as described above under different flow rate conditions and reference hematocrit. Referring to FIG. 8, it may be confirmed that the measurement error of each of the blood samples changed according to the shear rate did not exceed, at most, 10%. Therefore, in the case of the same blood samples as each other, there is no large difference between hematocrit measured by the apparatus for measuring hematocrit according to the present invention and hematocrit measured according to the related art.

Figure 9:
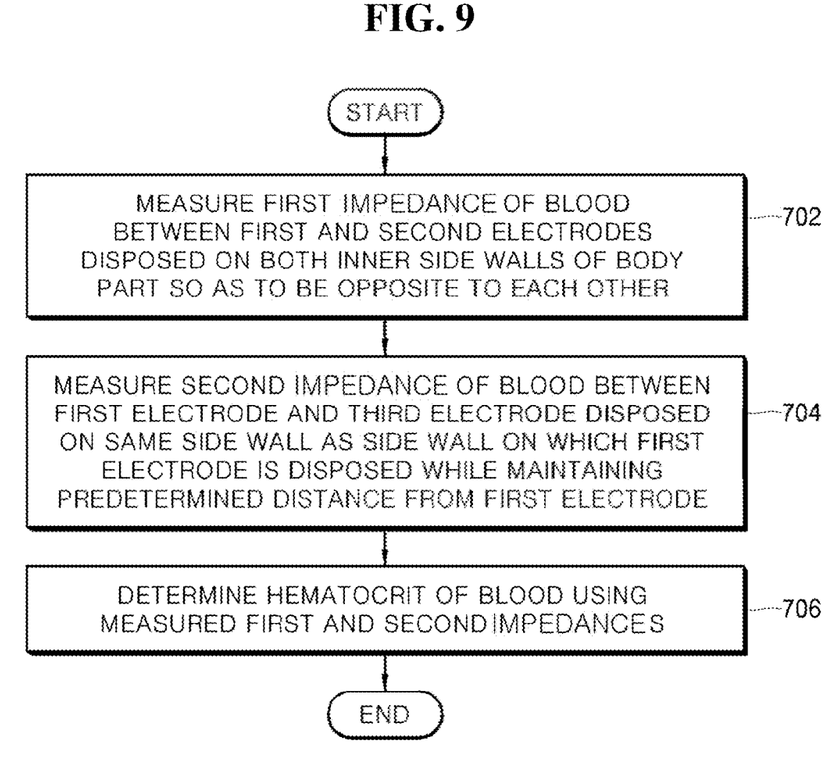
FIG. 9 is a flow chart of a method for measuring hematocrit of blood according to an exemplary embodiment of the present invention.

FIG. 9 is a flow chart of a method for measuring hematocrit of blood according to an exemplary embodiment of the present invention.

Referring to FIG. 9, first impedance of blood is measured between the first and second electrodes disposed on both inner side walls of the body part so as to be opposite to each other (702), and second impedance of the blood is measured between the first electrode and the third electrode disposed on the same side wall as the side wall on which the first electrode is disposed while maintaining a predetermined distance from the first electrode (704).

Then, hematocrit of blood is determined using the measured first and second impedances (706). In the exemplary embodiment of the present invention, the determining of the hematocrit of blood (706) includes calculating a first hematocrit estimation parameter using first impedance, calculating a second hematocrit estimation parameter using second impedance, and determining hematocrit using the first and second hematocrit estimation parameters. In addition, the determining of the hematocrit of blood (706) may further include determining a normalized difference using the first and second hematocrit estimation parameters and determining hematocrit using the first hematocrit estimation parameter and the normalized difference.

Here, the first impedance includes impedance of plasma of blood and impedance of cytoplasm of blood measured between the first and second electrodes, and the second impedance includes impedance of plasma of blood and impedance of cytoplasm of blood measured between the first and third electrodes.

In addition, the first or second hematocrit estimation parameter is determined by a ratio of the impedance of plasma and a sum of the impedance of plasma and the impedance of cytoplasm.

As set forth above, according to the present invention, hematocrit of flowing blood may be more simply and accurately measured in real time.

The present invention described above may be variously substituted, altered, and modified by those skilled in the art to which the present invention pertains without departing from the scope and sprit of the present invention. Therefore, the present invention is not limited to the above-mentioned exemplary embodiments and the accompanying drawings.

What is claimed is:

1. An apparatus for measuring hematocrit of blood, the apparatus comprising:
   a body part provided with a first inner side wall opposite a second inner sidewall, a blood inlet and a blood outlet;
   a first electrode disposed on the first inner side wall, and a second electrode disposed on the second inner side wall, wherein the first electrode and the second electrode are opposite to each other;
   a third electrode disposed on the first inner side wall and disposed a predetermined distance from the first electrode;
   a measurement unit configured to measure a first impedance of blood between the first and second electrodes and a second impedance of the blood between the first and third electrodes; and
   a calculation unit configured to determine hematocrit of blood using the first and second impedances, wherein the calculation unit is configured to calculate a first and a second hematocrit estimation parameter by determining a ratio of the impedance of plasma and a sum of the impedance of plasma and the impedance of cytoplasm, wherein the impedance of plasma and the impedance of cytoplasm of the blood are determined using the first and second impedance measurements, determining a normalized difference between the first and second hematocrit estimation parameters, and determining the hematocrit of the blood using both the first hematocrit estimation parameter and the normalized difference.

2. A method for measuring hematocrit of blood, the method comprising:
   measuring, using an apparatus comprising a body part provided with a first inner side wall opposite a second inner sidewall, a blood inlet and a blood outlet; a first electrode disposed on the first inner side wall, and a second electrode disposed on the second inner side wall, wherein the first electrode and the second electrode are opposite to each other; and a third electrode disposed on the first inner side wall and disposed a predetermined distance from the first electrode; a first impedance of blood between first and second electrodes;
   measuring a second impedance of the blood between the first electrode and a third electrode;
   calculating a first and a second hematocrit estimation parameter by determining a ratio of the impedance of plasma and a sum of the impedance of plasma and the impedance of cytoplasm, wherein the impedance of plasma and the impedance of cytoplasm of the blood are determined using the first and second impedance measurements, determining a normalized difference between the first and second hematocrit estimation parameters, and
   determining the hematocrit of the blood using both the first hematocrit estimation parameter and the normalized difference.

* * * * *